United States Patent
Chewter et al.

(10) Patent No.: US 9,067,860 B2
(45) Date of Patent: Jun. 30, 2015

(54) PROCESS FOR CONVERTING AN ALKYL TERT-ALKYL ETHER INTO AN ALKANOL AND AN ISO-ALKANE

(71) Applicant: SHELL OIL COMPANY, Houston, TX (US)

(72) Inventors: Leslie Andrew Chewter, Amsterdam (NL); Hervé Henry, Rotterdam (NL); Pieter Oldenhove, Amsterdam (NL); Rajaram Ramesh, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 285 days.

(21) Appl. No.: 13/653,149

(22) Filed: Oct. 16, 2012

(65) Prior Publication Data

US 2013/0096352 A1    Apr. 18, 2013

(30) Foreign Application Priority Data

Oct. 17, 2011    (EP) .................................... 11185470

(51) Int. Cl.
*C07C 29/00* (2006.01)
*C07C 29/132* (2006.01)
*C07C 1/20* (2006.01)

(52) U.S. Cl.
CPC .................. *C07C 29/132* (2013.01); *C07C 1/20* (2013.01); *C07C 2521/12* (2013.01); *C07C 2523/42* (2013.01)

(58) Field of Classification Search
CPC .............................. C07C 29/00; C07C 29/132
USPC ........................................................ 568/907
See application file for complete search history.

(56) References Cited

U.S. PATENT DOCUMENTS

2008/0058569 A1*  3/2008  Winterberg et al. .......... 585/639
2011/0118523 A1    5/2011  Winterberg et al.

OTHER PUBLICATIONS

Chauvel, A., et al.; "Petrochemical Processes Part 1. Synthesis-gas derivatives and major hydrocarbon"; Editions Technip; pp. 213-215;1989.
Fields, D.L., et al.; "Catalytic destrucion of methyl lertiary butyl ether (MTBE) with Pt/Rh monolithic automotive exhaust catalyst"; Applied Catalysis B:; Enviornmental 15; pp. 93-15; 1998.

* cited by examiner

*Primary Examiner* — Porfirio Nazario Gonzalez
*Assistant Examiner* — Kofi Adzamli

(57) ABSTRACT

The invention relates to a process for converting an alkyl tert-alkyl ether into an alkanol and an iso-alkane wherein the alkyl tert-alkyl ether is contacted with a hydrocracking catalyst in the presence of hydrogen under hydrocracking process conditions.

13 Claims, No Drawings

PROCESS FOR CONVERTING AN ALKYL TERT-ALKYL ETHER INTO AN ALKANOL AND AN ISO-ALKANE

This application claims the benefit of European Application No. 11185470.9 filed Oct. 17, 2011, which is incorporated herein by reference.

FIELD OF THE INVENTION

The invention relates to a process for converting an alkyl tert-alkyl ether into an alkanol and an iso-alkane.

BACKGROUND TO THE INVENTION

It is known that alkyl tert-alkyl ethers such as for example methyl tert-butyl ether, can be converted into an iso-alkene and an alkanol by an endothermic cracking reaction. A process for cracking of methyl tert-butyl ether into isobutene and methanol is for example disclosed in A. Chauvel and G. Lefebvre, Petrochemical Processes Part 1. Synthesis-gas derivatives and major hydrocarbon, 1989, Editions Technip, Paris, pp 213-215. The reaction takes place in the presence of an acid catalyst and is operated in the presence of steam.

It would be advantageous to convert methyl tert-butyl ether into isobutane instead of isobutene, since isobutane can be used as feed in for example alkylation processes. Isobutane can be obtained by hydrogenating isobutene obtained by cracking of methyl tert-butyl ether. A disadvantage, however, of cracking followed by hydrogenation is that two process steps are needed. One step being endothermic and the other one being exothermic.

SUMMARY OF THE INVENTION

It has now been found that alkyl tert-alkyl ethers can be directly converted in its corresponding alkanol and iso-alkane by contacting the alkyl tert-alkyl ether with a hydrocracking catalyst in the presence of hydrogen under hydrocracking process conditions.

Accordingly, the present invention relates to a process for converting an alkyl tert-alkyl ether into an alkanol and an iso-alkane wherein the alkyl tert-alkyl ether is contacted with a hydrocracking catalyst in the presence of hydrogen under hydrocracking process conditions.

An advantage of the process according to the invention is that iso-alkane can be directly obtained from alkyl tert-alkyl ether, i.e. without the need to make iso-alkene and/or tertiary-alkanol as intermediate product. Moreover, the present process can be carried out at conditions that are milder than the conditions needed for cracking of alkyl tert-alkyl ether. A further advantage is that hydrocracking is typically carried out in the absence of steam and therefore, no alkanol/water separation step is needed.

DETAILED DESCRIPTION OF THE INVENTION

In the process according to the invention, an alkyl tert-alkyl ether is converted into its corresponding alkanol and iso-alkane by contacting the alkyl tert-alkyl ether with a hydrocracking catalyst in the presence of hydrogen at hydrocracking process conditions. Preferably, the process is carried out in a reaction zone comprising a fixed bed of the hydrocracking catalyst. Such reactors comprising a fixed bed of catalyst are well-known in the art.

The alkyl tert-alkyl ether and hydrogen are supplied to the reaction zone. Preferably, a stoichiometric excess of hydrogen is used, i.e. the molar amount of hydrogen supplied to the reaction zone is larger than the molar amount of alkyl tert-alkyl ether supplied to the reaction zone. Preferably, the molar ratio of hydrogen and alkyl tert-alkyl ether supplied to the reaction zone is below 15, since a high ratio will lead to undesired loss of hydrogen in the case of conversion of an methyl tert-alkyl ether. More preferably, the molar ratio of hydrogen and alkyl tert-alkyl ether supplied to the reaction zone is in the range of from 1.05 to 7.0, even more preferably of from 1.1 to 5.0.

The process may be carried out with and without recycle of hydrogen. Preferably, the process is operated with a small stoichiometric excess of hydrogen, for example a molar ratio of hydrogen and alkyl tert-alkyl ether supplied to the reaction zone in the range of from 1.05 to 5.0 and in a once through mode, i.e. without recovery and recycle of hydrogen.

The process is carried out at hydrocracking process conditions. Reference herein to hydrocracking process conditions is to process conditions under which hydrocracking of alkyl tert-alkyl ether into alkanol and iso-alkane takes place. Preferably, the hydrocracking process conditions comprise a temperature of at most 200° C. Higher temperature will result in larger amounts of undesired by-products such as iso-alkene and dialkyl ether. More preferably, the temperature is in the range of from 50 to 200° C., even more preferably of from 60 to 180° C., still more preferably of from 80 to 150° C. A temperature in the range of from 85 to 120° C. is particularly preferred. Preferably, the hydrocracking process condition comprise a pressure at which the alkyl tert-alkyl ether is predominantly in the liquid phase. Reference herein to the alkyl tert-alkyl ether being predominantly in the liquid phase is to the alkyl tert-alkyl ether being for at least 80 wt %, preferably at least 90 wt % in the liquid phase. Preferably, the total pressure is in the range of from 1 to 35 bar (absolute).

In the process according to the invention, not only the iso-alkane corresponding to the tert-alkyl part of the ether is formed, but also an amount of the corresponding iso-alkene. In case the alkyl tert-alkyl ether is alkyl tert-butyl ether, both isobutane and isobutene are formed. The process conditions are preferably chosen such that the iso-alkane/iso-alkene equilibrium is towards iso-alkane. The equilibrium will inter alia depend on the stoichiometric excess of hydrogen and on the hydrocracking temperature. A higher temperature will shift the equilibrium towards iso-alkene. The conditions are preferably chosen such that an equilibrium towards iso-alkane is achieved with only a relatively small excess of hydrogen. For methyl tert-butyl ether, only a small excess of hydrogen is required at a temperature of 100° C. At higher temperatures, a larger excess of hydrogen is needed to shift the equilibrium towards iso-alkane.

Preferably, the conditions are chosen such that the ratio of iso-alkane to iso-alkene is as high as possible. Preferably, the molar ratio of iso-alkane to isobutene is at least 10, more preferably at least 50, even more preferably at least 100.

The process may be operated at a relatively high pressure, for example in the range of from 15 to 35 bar (absolute), such that the iso-alkane formed is in the liquid phase or at a relatively low pressure, for example in the range of from 1 to 15 bar (absolute), such that the iso-alkane formed is in the gas phase.

The process is preferably operated in liquid phase. If operated in liquid phase, the amount of hydrogen is preferably chosen sufficiently low to allow most and preferably all of the hydrogen to be dissolved in the liquid phase to avoid a separate gas phase.

The process may be operated either in upflow or in downflow configuration.

The liquid hourly space velocity (LHSV) is preferably in the range of from 1 to 50 h$^{-1}$, more preferably in the range of from 3 to 15 h$^{-1}$.

Further, the conditions are chosen such that skeletal isomerisation of iso-alkene into normal alkene is prevented. It will be appreciated that skeletal isomerisation will in increase with temperature, hydrogen pressure and acidity of the catalyst.

The alkyl tert-alkyl ether to be converted comprises a tertiary alkyl group and a further alkyl group that is preferably a primary alkyl group, more preferably a primary alkyl group with up to five carbon atoms, even more preferably a methyl or ethyl group. The tertiary alkyl group is preferably a tertiary-butyl group or a tertiary-pentyl group. A particularly preferred alkyl tert-alkyl ether is methyl tert-butyl ether.

Any suitable hydrocracking catalyst may be used in the process according to the invention. Such catalyst comprises a hydrogenating function, preferably a hydrogenating metal, supported on an acidic support material. Preferably, the catalyst comprises an acidic support material selected from zeolitic or amorphous silica alumina and alumina. Amorphous silica alumina is a particularly preferred support material. The hydrogenation function is preferably a hydrogenating metal selected from Group VIII metals, more preferably selected from Pt, Pd, Ru, Rh, Ir, Ni and combinations thereof. Particularly preferred hydrogenating metals are Pt, Pd, or a combination of Pt with Pd or Ru. In the case of conversion of a methyl tert-alkyl ether, a hydrogenating metal that does not easily convert methanol into carbon monoxide and hydrogen under the hydrocracking conditions prevailing in the process are particularly preferred. Examples of such hydrogenating metals are Pt, Pd, a combination of Pt and Ru, and sulphided Ni.

The hydrocracking catalyst is preferably pre-activated by reducing the catalyst with hydrogen prior to contacting the alkyl tert-alkyl ether with the catalyst. Such pre-activation is well-known in the art. Pre-activation may be carried out in-situ or ex-situ.

The alkyl tert-alkyl ether is contacted with the hydrocracking catalyst by supplying a feed stream comprising such ether to the catalyst. The feed stream may comprises small amounts of compounds other than alkyl tert-alkyl ether, such as for example methanol, other alkanols or water. The amount of water in the feed stream is preferably at most 5 wt % in order to avoid deactivation of the catalyst. Since hydrocracking catalyst will typically deactivate if they are contacted with large amounts of water, the process is typically carried out in the absence of steam.

Additionally to a feed stream comprising alkyl tert-alkyl ether, a stream comprising iso-alkene may be supplied to the hydrocracking catalyst in order to produce additional iso-alkane. Preferably, the iso-alkene corresponding to the iso-alkane produced is co-fed. In case the alkyl tert-alkyl ether is alkyl tert-butyl ether, it is advantageous to co-feed isobutene in order to increase the amount of isobutane produced. This is particularly advantageous in a situation wherein a waste stream of isobutene is available. This is for example the case if the process according to the invention is operated within a process line-up that also comprises a process for the conversion of methanol to olefins. In such process, not only the desired lower olefins, i.e. ethylene and propylene, are produced, but also isobutene as by-product.

EXAMPLES

The invention is illustrated by the following non-limiting examples.

Example 1

An amount of 100 mg of the 30-80 mesh sieve fraction of a catalyst comprising 0.8 (wt) % Pt on amorphous silica alumina was placed in a quartz reactor tube of 3.8 mm internal diameter. The tube was placed in an oven. The catalyst was reduced in-situ for 1 hour at 400° C. under atmospheric pressure with a gas consisting of hydrogen 50 (vol) % H2 and 50 (vol) % Ar. The reactor tube was subsequently cooled to a temperature of 50° C. and supplied with a flow of 50 ml/min of 50 (vol) % H2 and 50 (vol) % Ar. The tube was then heated to a hydrocracking temperature of 75° C. and fed with a feed containing 1.5 (vol) % MTBE vapour, 16.5 (vol) % H2 and the remainder Ar 50 ml/min. The composition of the reactor effluent was analyzed via mass spectroscopy.

Examples 2-4

Example 1 was repeated, but now at a hydrocracking temperature of 85° C. (Example 2), 95° C. (Example 3) and 105° C. (Example 4).

In the Table, the concentrations (in wt % based on total weight of the effluent) of isobutane, isobutene and methanol in the reactor effluent of Examples 1-4 is shown.

TABLE

| Composition of reactor effluent | | | | |
|---|---|---|---|---|
| Example | 1 | 2 | 3 | 4 |
| T (° C.) | 75 | 85 | 95 | 105 |
| Isobutane (wt %) | 33 | 56 | 59 | 58 |
| Isobutene (wt %) | <1 | <1 | <1 | <1 |
| Methanol (wt %) | 18 | 31 | 32 | 32 |

What is claimed is:

1. A process for directly converting an alkyl tert-alkyl ether into an alkanol and an iso-alkane in a single process step wherein the alkyl tert-alkyl ether is contacted with a hydrocracking catalyst in the presence of a stoichiometric excess of hydrogen under hydrocracking process conditions, wherein the hydrocracking catalyst comprises a hydrogenating metal selected from the group consisting of Pt, Pd, Ru, Rh, Ir, Ni and combinations thereof on an acidic support material.

2. A process according to claim 1, wherein the alkyl tert-alkyl ether is an alkyl tert-butyl ether and the iso-alkane is isobutane.

3. A process according to claim 1, wherein the alkyl tert-alkyl ether is a methyl or ethyl tert-alkyl ether.

4. A process according to claim 2 or claim 3, wherein the alkyl tert-alkyl ether is methyl tert-butyl ether.

5. A process according to claim 1, wherein the hydrogenating metal is Pt, Pd or a combination of Pt and Ru or Pd.

6. A process according to claim 1, wherein the acidic support material is amorphous silica alumina.

7. A process according to claim 5, wherein the acidic support material is amorphous silica alumina.

8. A process according to claim 1, wherein the hydrocracking process conditions comprise a temperature in the range of from 50 to 200° C.

9. A process according to claim 8, wherein the temperature is in the range of from 60 to 180° C.

10. A process according to claim 1, wherein the hydrocracking process conditions comprise a pressure in the range of from 1 to 35 bar (absolute).

11. A process according to claim 1, wherein an iso-alkene is co-fed to the hydrocracking catalyst.

12. A process according to claim 11, wherein the iso-alkene is the iso-alkene corresponding to the iso-alkane.

13. A process according to claim 12, wherein the iso-alkene is isobutene.

* * * * *